(12) United States Patent
Rosales et al.

US008287931B2

(10) Patent No.: US 8,287,931 B2
(45) Date of Patent: *Oct. 16, 2012

(54) NUTRITIONAL COMPOSITION TO PROMOTE HEALTHY DEVELOPMENT AND GROWTH

(75) Inventors: Francisco J. Rosales, Singapore (SG); Eric van Tol, Arnhem (NL); Gyan P. Rai, Newburgh, IN (US); Kristin Morris, Evansville, IN (US); Dattatreya Banavara, Newburgh, IN (US); Dirk Hondmann, Newburgh, IN (US); Zeina E. Jouni, Evansville, IN (US); Robert J. McMahon, Evansville, IN (US); Deborah A. Schade, Evansville, IN (US); Donald Carey Walker, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,981

(22) Filed: May 11, 2009

(65) Prior Publication Data

US 2010/0105615 A1 Apr. 29, 2010

Related U.S. Application Data

(63) Continuation of application No. 11/172,123, filed on Jun. 30, 2005, now Pat. No. 7,572,474, and a continuation of application No. 12/371,100, filed on Feb. 13, 2009, now Pat. No. 8,075,934.

(60) Provisional application No. 61/108,303, filed on Oct. 24, 2008, provisional application No. 61/111,009, filed on Nov. 4, 2008.

(51) Int. Cl.
*A23L 1/30* (2006.01)
(52) U.S. Cl. .......................................................... 426/72
(58) Field of Classification Search ........................ None
See application file for complete search history.

(56) References Cited

U.S. PATENT DOCUMENTS

| | | | |
|---|---|---|---|
| 4,859,488 A | 8/1989 | Kan et al. | |
| 5,437,880 A | 8/1995 | Takaichi et al. | |
| 5,461,033 A * | 10/1995 | Donnet et al. | 514/12 |
| 5,840,361 A | 11/1998 | Theuer et al. | |
| 5,952,295 A * | 9/1999 | Arnaud-Battandier et al. | 514/2 |
| 6,576,251 B1 | 6/2003 | Stahl et al. | |
| 6,706,287 B2 | 3/2004 | Ranganathan et al. | |
| 6,841,149 B1 | 1/2005 | Spangler et al. | |
| 2001/0022980 A1 | 9/2001 | Bell et al. | |
| 2002/0127211 A1 | 9/2002 | Brassart et al. | |
| 2003/0040492 A1 | 2/2003 | Haschke et al. | |
| 2003/0060445 A1 | 3/2003 | Wilson | |
| 2003/0072865 A1 | 4/2003 | Bindels et al. | |
| 2003/0129278 A1 | 7/2003 | Stahl et al. | |
| 2003/0157146 A1 | 8/2003 | Rautonen et al. | |
| 2004/0062758 A1 | 4/2004 | Mayra-Makinen et al. | |
| 2004/0071824 A1 | 4/2004 | Van Laere et al. | |
| 2004/0072794 A1 | 4/2004 | Kaup et al. | |
| 2004/0077539 A1 | 4/2004 | Maase | |
| 2004/0121042 A1 | 6/2004 | Kudo et al. | |
| 2004/0161422 A1 | 8/2004 | Ranganathan | |
| 2004/0191234 A1 | 9/2004 | Haschke et al. | |
| 2004/0191295 A1 | 9/2004 | Locniskar et al. | |
| 2004/0219157 A1 | 11/2004 | Rochat et al. | |
| 2005/0271641 A1 * | 12/2005 | Bjorksten et al. | 424/93.45 |
| 2006/0233915 A1 * | 10/2006 | Puski et al. | 426/72 |
| 2006/0240148 A1 | 10/2006 | Nguyen et al. | |
| 2006/0286210 A1 * | 12/2006 | Rangavajla et al. | 426/72 |
| 2008/0095752 A1 | 4/2008 | Chiang et al. | |

FOREIGN PATENT DOCUMENTS

| | | |
|---|---|---|
| CA | 2340103 | 2/2000 |
| WO | 2004026316 | 4/2004 |
| WO | 2005039319 | 5/2005 |
| WO | 2005039597 | 5/2005 |

OTHER PUBLICATIONS

Article online by Dairy Foods Magazine, Oct. 2003 by Donna Brooks entitled "Polydextrose for Adding Fiber." Online at://www.dairyfoods.com.
Article by Chinese Medical Journal, 2004, vol. 117 No. 6, pp. 927-931 by X. Ben et al. entitled "Supplementation of milk formula with galacto-oligosaccharides improves intestinal micro-flora and fermentation in term infants." Online at //www.cmj.org/information/full.asp?id=1655.
Article by Current Pharmaceutical Design, 2005, vol. 11, pp. 55-74 by M.J. Kullen et al. entitled "The Delivery of Probiotics and Prebiotics to Infants."
Article by Early Human Development, 2001, vol. 65 Suppl., pp. 43-52 by M. Rivero-Urgell et al. entitled "Olgiosaccharides: application in infant food."
Article by American Journal Clinical Nutrition, 2001, vol. 73 Suppl., pp. 444-450 by E. Isolauri et al. entitled "Probiotics: effects on immunity1-3."
Article by American Journal Clinical Nutrition, 2001, vol. 73 Suppl., pp. 415-420 by J. Cummings et al. entitled "Prebiotics digestion and fermentation1-3."
Article by American Society for Nutritional Sciences, Nutritional Immunology-Research Communication, 2003, pp. 153-156, by M. Roller et al. entitled "Prebiotic Inulin Enriched with Oligofructose in Combination with the Probiotic *Lactobacillus rhamnosus* and *Bifidobacterium lactis* Modulates Intestinal Immune Functions in Rats1."
Article from Journal of Medicinal Food, 2005, vol. 8(1), pp. 113-116 by Pylkans et al. entitled "Comparison of Different Fibers for In Vitro Production of short Chain Fatty Acids by Intestinal Microflora."

(Continued)

*Primary Examiner* — Cherie M Stanfield
(74) *Attorney, Agent, or Firm* — Waddey & Patterson, P.C.; James R. Cartiglia; Rebecca M. Barnett

(57) ABSTRACT

A nutritional composition for improving the immunological function of a subject, including a lipid or fat; a protein source; about 5 to about 100 mg/100 kcal of a source of long chain polyunsaturated fatty acids which comprises docosahexanoic acid; and about 0.1 to about 1 mg/100 kcal of a prebiotic composition, wherein the prebiotic composition comprises at least 20% of an oligosaccharide which has a fermentation rate which is demonstrably slower than that of galacto-oligosaccharide.

14 Claims, No Drawings

OTHER PUBLICATIONS

Article by Applied and Environmental Microbiology, Aug. 2004, vol. 70, No. 8, pp. 4505-4511 by H. Probert et al. entitled "Polydextros, Lactitol, and Fructo-Oligosaccharide Fermentation by Colonic Bacteria in a Three-Stage Continuous Culture System."

Article from Journal of Family Practice, Aug. 2002 by Mark R. Ellis entitled "What is the best therapy for constipation in infants?"— Clinical inquiries: from the Family Practice Inquiries Network. Online at //www.findarticles.com/p/articles/mi_m0689/is_8_51/ai_90464039/print.

Article from Am J Clin Nutr, 2000, vol. 72 pp. 1503-1509 by Zhong Jie, et al. entitled Studies on the effects of polydextrose intake on physiologic functions in Chinese people 1-3.

Article from Journal of Pediatric Gastroenterology and Nutrition, May 2001, vol. 32, pp. 534-541 by Tianan Jiang et al. entitled "Gas Production by Feces of Infants."

Article from Journal of Pediatric Gastroenterology and Nutrition, Nov. 2004, vol. 39, pp. 465-473 by Carlo Agostoni, et al. entitled "Prebiotic Oligosaccharides in Dietetic Products for Infants: A Commentary" by the ESPGHAN Committee on Nutrition.

Article by Nutrition, 2002, vol. 18, pp. 484-489 by Pedro A. Alarcon et al. entitled "Gastrointestinal Tolerance of a New Infant Milk Formula in Healthy Babies: An International Study Conducted in 17 Countries."

Article from J. Clin Gastroenteroal, Jul. 2004, vol. 38, Supp. 2 pp. S76-S79 by G. Boehm et al. entitled "Prebiotic in Infant Formulas."

Article from Acta Paediatrica, 2005, vol. 94 (Suppl. 449), pp. 18-21 by Gunther Boehm et al. entitled "Prebiotic.Carbohydrates in Human Milk and Formulas."

Article from Arch. Dis. Child. Fetal Neonatal Ed., 2002, vol. 86, pp. F178-F181 by G. Boehm et al. entitled Supplementation of a bovine milk formula with an oligosaccharide mixture increases counts of faecal bifidobacteria in preterm infants. Online at http://www.bmj-journals.com.

ESPGHAN Abstracts by J. Pediatr Gastroenterology Nutr., Apr. 2003, vol. 36(4), No. P179 by G. Boehm et al. entitled Effect of increasing number of intestinal bifidobacteria on the presence of clinically relevant pathogens.

Article from Pediatrics, May 1993, vol. 91, No. 5, pp. 908-914 by Christi K. Bradley et al. entitled "Evaluation of Two Iron-Fortified, Milk-Based Formulas During Infancy."

Article from Pediatric Research, 2006, vol. 59, No. 3, pp. 451-456 by Oscar Brunser et al. entitled "Effect of Milk Formula with Prebiotics on the Intestinal Microbiota of Infants After an Antibiotic Treatment."

Article from Journal of Pediatric Gastroenterology and Nutrition, 2000, vol. 30, pp. 181-192 by Renee M. Erney et al. entitled "Variability of Human Milk Neutral Oligosaccharides in a Diverse Population."

Article from Acta Paediatr, 2003, Supp. 441, pp. 48-55 by S. Fanaro et al. entitled "Intestinal Microflora in Early Infancy: Composition and Development."

Article from Journal of Pediatric Gastroenterology and Nutrition, Aug. 2005, vol. 41, pp. 186-190 by S. Fanaro et al. entitled "Acidic Oligosaccharides from Pectin Hydrolysate as New Component for Infant Formulai: Effect on Intestinal Flora, Stool Characteristics, and pH."

Article from J. Nutr., 1989, vol. 129, pp. 1438S-1441S by Glenn R. Gibson entitled "Dietary Modulation of the Human Gut Microflora Using the Prebiotics Oligofructose and Inulin."

Article from J. Nutr., 1995, vol. 125, pp. 1401-1412 by Glenn R. Gibson et al. entitled "Dietary Modulation of the Human Colonic Microbiota: Introducing the Concept of Prebiotics."

Article fromPediatrics, 1995, vol. 95, pp. 50-54 by Jeffrey S. Hyam et al. entitled "Effect of Infant Formula on Stool Characteristics of Young Infants."

Article from Journal of Pediatric Gastroenterology and Nutrition, Mar. 2003, vol. 36, pp. 301-310 by Lawrence T. Weaver entitled "Improving Infant Milk Formulas: Near the End of the Trail for the Holy Grail?"

Article from Microbiol. Immunol., 1984, vol. 28, No. 9, pp. 975-986 by Yoshimi Benno et al. entitled "The Intestinal Microflora of Infants: Composition of Fecal Flora in Breast-Fed and Bottle-Fed Infants."

ESPGHAN Abstracts from Journal of Pediatric Gastroenterology and Nutrition, Apr. 2002, vol. 34(4), p. 477, No. 2 by Knol et al. entitled "Bifidobacterial species that are present in breast fed infants are stimulated in formula fed infants by changing to a formula containing prebiotics."

Article from Lipids, 1991, vol. 26, pp. 250-253 by R.J. Jandacek entitled "The Solubilization of Calcium Soaps by Fatty Acids."

Article from Journal Clinical Microbiology, Feb. 1987, pp. 285-289 by Elisabeth A.E. Mevisen, et al. entitled "*Bifidobacterium, Bacteroides*, and *Clostridium* spp. In Fecal Samples from Breast-Fed and Bottle-Fed Infants with and without Iron Supplement."

A book entitled Handbook of Milk Composition (1995) published by Academic Press, San Diego, Chapter 4, pp. 273-349, by David S. Newburg et al. entitled "Carbohydrates in Milks" Analysis, Quantities and Significance.

Article by The EFSA Journal, 2004, vol. 31, pp. 1-11 entitled "Opinion of the Scientific Panel on Dietetic Products, Nutrition and Allergies on a request from the Commission relating to the safety and suitability for particular nutritional use by infants of fructooligosaccharides in infant formulae and follow-on formulae."

Article by Am J Clin Nutr, 1999, vol. 70, pp. 920-927 by Kathy Kennedy et al. entitled "Double-blind, randomized trial of a synthetic triacylglycerol in formula-fed term infants: effects on stool biochemistry, stool characteristics, and bone mineralization 1-3."

ESPR Abstracts from J. Pediatr Gastroenterol Nutr., 2005, p. 487, Abstract No. 134 by C. van Limpt et al. entitled "Effect of Colonic Short Chain Fatty Acids, Lactate and pH on the Growth of Common Gut Pathogens."

Article by Pediatrics, Jan. 1999, vol. 103, No. 1, pp. 1-6 by Beate Lloyd et al. entitled "Formula Tolerance in Postbreastfed and Exclusively Formula-fed Infants."

Article by Acta Paediatr Scand., 1985, vol. 74, pp. 45-51 by B. Lundequest, et al. entitled "The Composition of the Faecal Microflora in Breastfed and Bottle Fed Infants from Birth to Eight Weeks."

Article by BMJ, 1999, vol. 318, pp. 999-1003 by George T. Macfarlane et al. entitled "Probiotics and prebiotics: can regulating the activities of intestinal bacteria benefit health?"

A review published in Geneva 1994 by Gordon & Breach Science, pp. 90-106, Chapter 5 by Keisuke Matsumoto et al. entitled "Galactooligosaccharides."

Article by Child: Care, Health and Development, 1997, vol. 23, No. 6, pp. 475-478 by R. Morley et al. entitled Infant Feeding and maternal concerns about stool harness.

Article by Acta Paediatr, 2003, Suppl. 441, pp. 77-79 by GE Moro, et al. entitled "Effects of a new mixture of prebiotics on faecal flora and stools in term infants."

Article by Acta Paediatrica, 2005, vol. 94, Suppl. 449, pp. 27-30 by Guido Moro et al. entitled Dietary prebiotic oligosaccharides are detectable in the faeces of formula-fed infants.

Article by Acta Paediatr, 1999, Suppl. 430, pp. 47-57 by K. Orrhage et al. entitled "Factors controlling the bacterial colonization on the intestine in breastfed infants."

Article by Journal of Pediatric Gastroenterology and Nutrition, 1995, vol. 20, pp. 81-90 by P.T. Quinlan et al. entitled "The Relationship between Stool Hardness and Stool Composition in Breast and Formula-Fed Infants."

Article from Immunology and Medical Microbiology, 2005, vol. 43, pp. 59-65 by Minna M. Rinne et al. entitled "Similar bifidogenic effects of prebiotic-supplemented partially hydrolyzed infant formula and breastfeeding on infant gut microbiota."

Article by Eur J. Nutr, 2002, vol. 41, pp. 85-92 by Silvia Rudloff et al. entitled "Detection of ligands for selectins in the oligosaccharide fraction of human milk."

Article by Am J Clin Nutr, 2001, vol. 73 (Suppl.), pp. 459S-464S by Katharina E. Scholz-Ahrens et al. entitled "Effects of prebiotics on mineral metabolism."

Abstract from PubMed by Indian J. Matern Child Health, 1993, vol. 4, No. 2, pp. 62-63 by K. Singh et al. entitled "Mothers' concept of the ideal number, colour and consistency of stools of their infants." Online at www.ncbi.nlm.nig.gov/entrez/query.fcgi?CMD=search&DB=pubmed.

Article by British Journal of Nutrition, 1999, vol. 81, pp. 121-132 by Jan Van Loo et al. entitled "Functional food properties of non-digestible oligosaccharides: a consensus report from the ENDO project (DGXII AIRII-CT94-1095)."

Article from J Nutr, 1979, vol. 109, pp. 1682-1687 by Fred H. Mattson et al. entitled "The absorbability by Rats of Various Triglycerides of Stearic and Oleic Acid and the Effect of Dietary Calcium and Magnesium." Online at //jn.nutrition.org/cgi/content/abstract/109/10/1682.

Craig, S.A.S., et al., Polydextrose as Soluble Fiber: Physiological and Analytical Aspects, Cereal Foods World, vol. 43, No. 5, p. 370-376, May 1998.

Moro, G., et al., Dosage-Related Bifidogenic Effects of Galacto- and Fructooligosaccharides in Formula-Fed Term Infants, J. Pediatr Gastroenterol Nutr, vol. 34, No. 3, Mar. 2002.

Roberfroid, M.B., Health benefits of non-digestible oligosaccharides, Adv Exp Med Biol. 1997;427:211-9. Review. PubMed PMID: 9361846. Abstract only.

Boler, B. et al. "Carbohydrate blended with polydextrose lower gas production and short-chain fatty acid production in an in vitro system," Nutrition Research 29 (2009) 631-639.

Hernot, D. et al. "In Vitro Fermentation Profiles, Gas Production Rates, and Microbiota Modulation as Affected by Certain Fructans, Galactooligosaccharides, and Polydextrose," J. Agric Food Chem., 2009, 57 (4), 1354-1361.

Notice of Opposition to European Patent Application No. 1887888.

* cited by examiner

NUTRITIONAL COMPOSITION TO PROMOTE HEALTHY DEVELOPMENT AND GROWTH

RELATED APPLICATIONS

This application claims priority under 35 U.S.C. §120 from (a) copending and commonly assigned U.S. patent application Ser. No. 12/371,100, entitled Nutritional Composition With Improved Digestibility, filed Feb. 13, 2009, which in turn claims priority under 35 U.S.C. §119(e) from U.S. Provisional Patent Application Ser. No. 61/108,303 filed Oct. 24, 2008 and 61/111,009 filed Nov. 4, 2008, and (b) copending and commonly assigned U.S. patent application Ser. No. 11/172,123, entitled Method For Simulating The Functional Attributes of Human Milk Oligosaccharides In Composition-Fed Infants, filed Jun. 30, 2005, the disclosures of each of which are incorporated by reference herein.

TECHNICAL FIELD

This disclosure relates generally to the field of nutritional compositions. More particularly, the disclosure relates to a nutritional composition which provides improved digestibility, as compared to conventional compositions.

BACKGROUND

The gut microflora of a human is a complex collection of interrelated microbes which act together to facilitate the digestive process. In the case of infants, the gut microflora is rapidly established in the first few weeks following birth. The nature of this intestinal colonization is initially determined by early exposure to environmental sources of microbes as well as the health of the infant. Whether the infant is breast-fed or composition fed also has a strong influence on the intestinal bacterial population.

In the breast-fed infant, for example, *Bifidobacterium* spp. dominate among intestinal bacteria, with *Streptococcus* spp. and *Lactobacillus* spp. as less common contributors. In contrast, the microflora of formula-fed infants is more diverse, containing *Bifidobacterium* spp. and *Bacteroides* spp. as well as the more pathogenic species, *Staphylococcus, Escherichia coli* and *Clostridia*. The varied species of *Bifidobacterium* in the stools of breast-fed and formula-fed infants differ as well.

*Bifidobacteria* are generally considered "beneficial" bacteria and are known to protect against colonization by pathogenic bacteria. This likely occurs through competition for cell surface receptors, competition for essential nutrients, production of anti-microbial agents, and production of inhibitory compounds such as short chain fatty acids (SCFA) which may decrease fecal pH and inhibit potentially pathogenic bacteria.

*Bifidobacteria* are also associated with resistance to gastrointestinal (GI) tract and respiratory infection as well as an enhanced immune function, especially in children and infants. Therefore, the promotion of an intestinal environment in which *Bifidobacteria* dominate has become a goal in the development of nutritional compositions, including nutritional formulations for adults and children and compositions for formula-fed infants.

Human milk (HM) contains a number of factors that may contribute to the growth and population of *Bifidobacteria* in the gut microflora of infants. Among these factors is a complex mixture of more than 130 different oligosaccharides that reach levels as high as 8-12 g/L in transitional and mature milk. Kunz, et al., *Oligosaccharides in Human Milk: Structure, Functional, and Metabolic Aspects*, Ann. Rev. Nutr. 20: 699-722 (2000). These oligosaccharides are resistant to enzymatic digestion in the upper gastrointestinal tract and reach the colon intact, where they serve as substrates for colonic fermentation.

HM oligosaccharides are believed to elicit an increase in the number of *Bifidobacteria* in the colonic flora, along with a reduction in the number of potentially pathogenic bacteria. Kunz, et al., *Oligosaccharides in Human Milk: Structure, Functional, and Metabolic Aspects*, Ann. Rev. Nutr. 20: 699-722 (2000); Newburg, *Do the Binding Properties of Oligosaccharides in Milk Protect Human Infants from Gastrointestinal Bacteria?*, J. Nutr. 217:S980-S984 (1997). One way that HM oligosaccharides may increase the number of *Bifidobacteria* and reduce the number of potentially pathogenic bacteria is by acting as competitive receptors and inhibiting the binding of pathogens to the cell surface. Rivero-Urgell, et al., *Oligosaccharides: Application in Infant Food*, Early Hum. Dev. 65(S):43-52 (2001).

In addition to reducing the number of pathogenic bacteria and promoting the population of *Bifidobacteria*, when HM oligosaccharides are fermented, they produce SCFAs such as acetic, propionic and butyric acids. These SCFAs are believed to contribute to caloric content, serve as a major energy source for the intestinal epithelium, stimulate sodium and water absorption in the colon, and enhance small bowel digestion and absorption. In addition, SCFA are believed to contribute to overall gastrointestinal health by modulating gastrointestinal development and immune function.

The fermentation of HM oligosaccharides also reduces fecal ammonia, amine, and phenol concentrations, which have been implicated as the major odorous components of feces. Cummings & Macfarlane, *The Control and Consequences of Bacterial Fermentation in the Human Colon*, J. Appl. Bacteriol. 70:443-459 (1991); Miner & Hazen, *Ammonia and Amines: Components of Swine-Building Odor* ASAE 12:772-774 (1969); Spoelstra, *Origin of Objectionable Components in Piggery Wastes and the Possibility of Applying Indicator Components for Studying Odour Development*, Agric. Environ. 5:241-260 (1980); O'Neill & Phillips, *A Review of the Control of Odor Nuisance from Livestock Buildings: Part 3. Properties of the Odorous Substances which have been Identified in Livestock Wastes or in the Air Around them* J. Agric. Eng. Res. 53:23-50 (1992).

As a result of the oligosaccharides present in HM, the SCFA profile of a breast-fed infant is very different from that of a formula-fed infant. For example, breast-fed infants produce virtually no butyrate, with acetate comprising approximately 96% of the total SCFA production. Lifschitz, et al., *Characterization of Carbohydrate Fermentation in Feces of Composition-Fed and Breast-Fed Infants*, Pediatr. Res. 27:165-169 (1990); Siigur, et al., *Faecal Short-Chain Fatty Acids in Breast-Fed and Bottle-Fed Infants*. Acta. Paediatr. 82:536-538 (1993); Edwards, et al., *Faecal Short-Chain Fatty Acids in Breast-Fed and Formula-Fed Babies*, Acta. Paediatr. 72:459-462 (1994); Parrett & Edwards, *In Vitro Fermentation of Carbohydrates by Breast Fed and Formula Fed Infants*, Arch. Dis. Child 76:249-253 (1997). In contrast, while formula-fed infants also have acetate (74%) as the major SCFA in feces, they have considerable amounts of propionate (23%) and small amounts of butyrate (3%) present as well. These differences between the SCFA profiles of breast-fed infants and formula-fed infants could affect the energy, digestion, and overall health of the formula-fed infant.

Because cow's milk and commercially available infant formulas that are based on cow's milk provide only trace amounts of oligosaccharides, prebiotics are often used to supplement the diet of formula-fed infants. Prebiotics have been defined as "non-digestible food ingredients that beneficially affect the host by selectively stimulating the growth and/or activity of one or a limited number of bacteria in the colon that can improve the health of the host". Gibson, G. R. & Roberfroid, M. B., *Dietary Modulation of the Human Colonic Microbiota-Introducing the Concept of Probiotics*, J. Nutr. 125:1401-1412 (1995). Common prebiotics include fructo-oligosaccharide, gluco-oligosaccharide, galacto-oligosaccharide, isomalto-oligosaccharide, xylo-oligosaccharide and lactulose.

The incorporation of various prebiotic ingredients into infant formulas has been disclosed. For example, U.S. Patent App. No. 2003/0072865 to Bindels, et al. discloses an infant formula with an improved protein content and at least one prebiotic. The prebiotic component can be lacto-N-tetaose, lacto-N-fuco-pentaose, lactulose (LOS), lactosucrose, raffinose, galacto-oligosaccharide (GOS), fructo-oligosaccharide (FOS), oligosaccharides derived from soybean polysaccharides, mannose-based oligosaccharides, arabino-oligosaccharides, xylo-oligosaccharides, isomalto-oligo-saccharides, glucans, sialyl oligosaccharides, and fuco-oligosaccharides.

Similarly, U.S. Patent App. No. 2004/0191234 to Haschke discloses a method for enhancing the immune response which comprises administering at least one prebiotic. The prebiotic can be an oligosaccharide produced from glucose, galactose, xylose, maltose, sucrose, lactose, starch, xylan, hemicellulose, inulin, or a mixture thereof. The prebiotic can be present in an infant cereal.

In addition, other factors present in human breast milk are believed to be beneficial to the developing body. For instance, functional proteins such as transforming growth factor-beta (TGF-β) play a significant role in many processes necessary for health and development, in infants and children, as well as adults.

More specifically, TGF-β is the general name for a family of polypeptides, the members of which have multifunctional regulatory activities. Three differentially regulated mammalian isoforms (termed TGF-β1, TGF-β2 and TGF-β3) play important roles in a multitude of processes in the developing infant, child and adult. TGF-β is a 25-kDa homodimeric cytokine known to mediate pleitropic functions both within the immune system and systemically, it is expressed in several cell types in the intestinal mucosal including lymphocytes, epithelial cells, macrophages, and stromal cells as well as by T-cells, neutrophils, macrophages, epithelial cells, fibroblasts, platelets, osteoblasts, osteoclasts and others. In addition, TGF-β is present in human breast milk and may influence multiple aspects of infant health and development.

Accordingly, it would be beneficial to provide a nutritional composition which provides a combination of nutrients designed to encourage healthy development and growth, especially in an infant. Included in the nutritional composition should be a prebiotic substance that simulates the functional attributes of human milk oligosaccharides in infants, such as an increase in the population and species of beneficial bacteria in the infant gut and production of a SCFA profile similar to that of a breast-fed infant. Additionally, the nutritional composition should be well tolerated in animals, especially human infants and should not produce or cause excess gas, abdominal distension, bloating or diarrhea.

BRIEF SUMMARY

Briefly, the present disclosure is directed, in an embodiment, to a nutritional composition comprising a lipid or fat, a protein source, a source of long chain polyunsaturated fatty acids which include docosahexanoic acid (DHA), a prebiotic composition having at least 20% of an oligosaccharide which has a fermentation rate which is demonstrably slower than that of galacto-oligosaccharide. In some embodiments, the composition further includes a functional protein such as TGF-β. Moreover, in certain embodiments, the prebiotic comprises polydextrose.

The invention is also directed to a nutritional product comprising:

a. up to about 7 g/100 kcal of a fat or lipid, more preferably about 3 to about 7 g/100 kcal of a fat or lipid;

b. up to about 5 g/100 kcal of a protein source, more preferably about 1 to about 5 g/100 kcal of a protein source;

c. about 5 to about 100 mg/100 kcal of a source of long chain polyunsaturated fatty acids which include DHA, more preferably about 10 to about 50 mg/100 kcal of a source of long chain polyunsaturated fatty acids which include DHA; and d. about 1.0 to about 10.0 g/L of a prebiotic composition having at least 20% of an oligosaccharide which has a fermentation rate which is demonstrably slower than that of galacto-oligosaccharide, more preferably about 2.0 g/L to about 8.0 g/L of a prebiotic composition having at least 20% of an oligosaccharide which has a fermentation rate which is demonstrably slower than that of galacto-oligosaccharide.

In yet another embodiment, the invention is directed to a nutritional composition having improved digestibility, the composition comprising a lipid or fat, a protein source, a source of long chain polyunsaturated fatty acids which include docosahexanoic acid (DHA), and a prebiotic composition having at least 20% of an oligosaccharide an oligosaccharide which has a fermentation rate which is demonstrably slower than that of galacto-oligosaccharide.

DETAILED DESCRIPTION

One of the problems to be solved by the present invention is to provide novel nutritional products that are easily digested, provide physiochemical benefits, and/or provide physiological benefits. In an embodiment of the present invention, a nutritional composition comprises a lipid or fat, a protein source, a source of long chain polyunsaturated fatty acids which include docosahexanoic acid (DHA), a prebiotic composition having at least 20% of an oligosaccharide which has a fermentation rate which is demonstrably slower than that of galacto-oligosaccharide, and, optionally, TGF-β. In certain embodiments, the prebiotic comprises polydextrose, and can be a combination of polydextrose and galacto-oligosaccharide. More particularly, the composition disclosed herein comprises:

a. up to about 7 g/100 kcal of a fat or lipid, more preferably about 3 to about 7 g/100 kcal of a fat or lipid;

b. up to about 5 g/100 kcal of a protein source, more preferably about 1 to about 5 g/100 kcal of a protein source;

c. about 5 to about 100 mg/100 kcal of a source of long chain polyunsaturated fatty acids which include DHA, more preferably about 10 to about 50 mg/100 kcal of a source of long chain polyunsaturated fatty acids which include DHA; and d. about 1.0 to about 10.0 g/L of a prebiotic composition having at least 20% of an oligosaccharide which has a fermentation rate which is demonstrably slower than that of galacto-oligosaccharide, more preferably about 2.0 g/L to about 8.0 g/L of a prebiotic composition having at least 20% of an oligosaccharide which has a fermentation rate which is demonstrably slower than that of galacto-oligosaccharide.

In an embodiment, the composition further includes about 0.015 to about 0.1 (pg/μg) ppm TGF-β, more preferably about 0.0225 to about 0.075 (pg/μg) ppm TGF-β.

In some embodiments, the nutritional composition may be an infant formula. As used herein, the term "infant" means a person not more than 12 months of age. The term "infant formula" applies to a composition in liquid or powdered form that satisfies the nutrient requirements of an infant by being a substitute for human milk. In the United States, the content of an infant formula is dictated by the federal regulations set forth at 21 C.F.R. §§100, 106 and 107. These regulations define macronutrient, vitamin, mineral, and other ingredient levels in an effort to simulate the nutritional and other properties of human breast milk. In a separate embodiment, the nutritional product may be a human milk fortifier, meaning it is a composition which is added to human milk in order to enhance the nutritional value of human milk. As a human milk fortifier, the inventive composition may be in powder or liquid form. In yet another embodiment, the inventive nutritional product may be a children's nutritional composition. As used herein, the term "young child" or "young children" means persons more than 12 months of age up to the age of three years (36 months). The term "child" or "children" as used herein means persons over the age of 3 years and prior to adolescence.

The nutritional products of the invention may provide minimal, partial, or total nutritional support. The compositions may be nutritional supplements or meal replacements. In some embodiments, the compositions may be administered in conjunction with a food or nutritional composition. In this embodiment, the compositions can either be intermixed with the food or other nutritional compositions prior to ingestion by the subject or can be administered to the subject either before or after ingestion of a food or nutritional composition. The compositions may be administered to preterm infants receiving infant formula, breast milk, a human milk fortifier, or combinations thereof. The term "preterm infants" or "premature infants" as used herein means infants born after less than 37 weeks gestation. In one embodiment, the composition is administered to preterm infants as an enteral nutritional supplement.

The compositions may, but need not, be nutritionally complete. The skilled artisan will recognize "nutritionally complete" to vary depending on a number of factors including, but not limited to, age, clinical condition, and dietary intake of the subject to whom the term is being applied. In general, "nutritionally complete" means that the nutritional composition of the present invention provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The composition which is "nutritionally complete" for the preterm infant will, by definition, provide qualitatively and quantitatively adequate amounts of all carbohydrates, lipids, essential fatty acids, proteins, essential amino acids, conditionally essential amino acids, vitamins, minerals, and energy required for growth of the preterm infant. The composition which is "nutritionally complete" for the term infant will, by definition, provide qualitatively and quantitatively adequate amounts of all carbohydrates, lipids, essential fatty acids, proteins, essential amino acids, conditionally essential amino acids, vitamins, minerals, and energy required for growth of the term infant. The skilled artisan will recognize the term "term infant" as referring to infants born after at least 37 weeks gestation and, commonly, between 37 and 42 weeks gestation. The composition which is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child given the specific age and developmental stage of said child.

The nutritional composition may be provided in any form known in the art, including a powder, a gel, a suspension, a paste, a solid, a liquid, a liquid concentrate, or a ready-to-use product. In one preferred embodiment, the nutritional composition is an infant composition, especially an infant composition adapted for use as sole source nutrition for an infant. In another embodiment, the nutritional composition is adapted for use as sole source nutrition for preterm infants. In other embodiments, the nutritional composition may be a follow-up formula, a growing-up milk, a milk modifier and combinations thereof.

In the preferred embodiments, the nutritional product disclosed herein may be administered enterally. As used herein, "enteral" means through or within the gastrointestinal, or digestive, tract, and "enteral administration" includes oral feeding, intragastric feeding, transpyloric administration, or any other introduction into the digestive tract.

Suitable fat or lipid sources for practicing the present invention may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

Bovine milk protein sources useful in practicing the present invention include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins are provided as intact proteins. In other embodiments, the proteins are provided as a combination of both intact proteins and partially hydrolyzed proteins, with a degree of hydrolysis of between about 4% and 10%. In yet another embodiment, the protein source may be supplemented with glutamine-containing peptides.

In a particular embodiment of the invention, the whey:casein ratio of the protein source is similar to that found in human breast milk. In an embodiment, the protein source comprises from about 40% to about 80% whey protein. In another embodiment, the protein source may comprise from about 20% to about 60% caseins.

In one embodiment of the invention, the nutritional composition may contain one or more probiotics. The term "probiotic" means a microorganism that exerts beneficial effects on the health of the host. Any probiotic known in the art may be acceptable in this embodiment provided it achieves the intended result. In a particular embodiment, the probiotic may be selected from *Lactobacillus* species, *Lactobacillus rhamnosus* GG, *Bifidobacterium* species, *Bifidobacterium longum*, and *Bifidobacterium animalis* subsp. *lactis* BB-12.

If included in the composition, the amount of the probiotic may vary from about $10^4$ to about $10^{10}$ colony forming units (cfu) per kg body weight per day. In another embodiment, the amount of the probiotic may vary from about $10^6$ to about $10^9$ cfu per kg body weight per day. In yet another embodiment, the amount of the probiotic may be at least about $10^6$ cfu per kg body weight per day.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated but retain the ability to favorably influence the health of the host. The probiotics useful in the present invention may be naturally-occurring, synthetic or developed through the genetic manipulation of organisms, whether such new source is now known or later developed.

The nutritional composition contains one or more prebiotics. The term "prebiotic" as used herein refers to indigestible food ingredients which exert health benefits upon the host. Such health benefits may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present invention may include oligosaccharides, polysaccharides, and other prebiotics that contain fructose, xylose, soya, galactose, glucose and mannose. More specifically, prebiotics useful in the present invention may include lactulose, lactosucrose, raffinose, gluco-oligosaccharide, inulin, polydextrose, polydextrose powder, fructo-oligosaccharide, isomalto-oligosaccharide, soybean oligosaccharides, lactosucrose, xylo-oligosacchairde, chito-oligosaccharide, manno-oligosaccharide, aribino-oligosaccharide, siallyl-oligosaccharide, fuco-oligosaccharide, and gentio-oligosaccharides, galacto-oligosaccharide.

In an embodiment, the total amount of prebiotics present in the nutritional composition may be from about 1.0 g/L to about 10.0 g/L of the composition. As noted, the total amount of prebiotics present in the nutritional composition may be from about 2.0 g/L and about 8.0 g/L of the composition. At least 20% of the prebiotics should comprise an oligosaccharide which has a fermentation rate which is demonstrably slower than that of galacto-oligosaccharide.

The inclusion of comprise an oligosaccharide which has a fermentation rate which is demonstrably slower than that of galacto-oligosaccharide, such as polydextrose (PDX), functions to decrease the rate and extent of fermentation of prebiotics within the gut, which facilitates tolerance, especially in infants, and simulates the functional attributes of human milk oligosaccharides, providing a short chain fatty acid profile similar to that of a breast-fed infant.

Polydextrose is a non-digestible carbohydrate that can be synthesized from randomly cross-linked glucose and sorbitol. It is not digested in the upper gastrointestinal (GI) tract, and is only partially fermented in the lower GI tract, making it a beneficial ingredient for digestive health. The physiological benefits of polydextrose include increased fecal bulk, reduced transit time, reduced fecal pH and reduced concentration of putrefactive substances in the colon. In the infant gut, polydextrose is primarily metabolized to acetate and propionate, with little butyrate formation (butyrate has been associated with harmful effects if produced at significant levels in the infant intestine); in adults, polydextrose has been shown to increase the production of acetate and butyrate.

In addition to polydextrose, the prebiotic composition can also comprise galacto-oligosacchardie (sometimes referred to as trans-galacto-oligosaccharide, or GOS), which has been described as a mixture of D-glucose and D-galactose. If galacto-oligosaccharide is used as a prebiotic, the amount of galacto-oligosaccharide in the nutritional composition may, in an embodiment, be within the range of from about 1.0 g/L to about 4.0 g/L.

The amount of polydextrose in the nutritional composition may, in an embodiment, be from about 0.2 mg/100 Kcal to about 1.0 mg/100 Kcal. In another embodiment, the amount of polydextrose in the nutritional composition may be from about 0.1 mg/100 Kcal to about 0.5 mg/100 Kcal. If galacto-oligosaccharide is used as a prebiotic, the amount of galacto-oligosaccharide in the nutritional composition may, in an embodiment, be within the range of from about 0.1 mg/100 Kcal to about 0.5 mg/100 Kcal. In a particular embodiment, polydextrose and galacto-oligosaccharide are supplemented into the nutritional composition in a total amount of about 0.6 mg/100 Kcal.

The nutritional composition of the invention contains a source of long chain polyunsaturated fatty acids (LCPUFAs) which comprise docosahexanoic acid (DHA). Other suitable LCPUFAs include, but are not limited to, α-linoleic acid, γ-linoleic acid, linoleic acid, linolenic acid, eicosapentanoic acid (EPA) and arachidonic acid (ARA).

In one embodiment, the nutritional composition is supplemented with both DHA and ARA. In this embodiment, the weight ratio of ARA:DHA may be from about 1:3 to about 9:1. In one embodiment of the present invention, this ratio is from about 1:2 to about 4:1.

The amount of long chain polyunsaturated fatty acids in the nutritional composition may vary from about 5 mg/100 kcal to about 100 mg/100 kcal, more preferably from about 10 mg/100 kcal to about 50 mg/100 kcal.

The nutritional composition may be supplemented with oils containing DHA and ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

In a particular embodiment, the composition of the invention is a milk-based nutritional composition which provides physiochemical and physiological benefits. As is known in the art, bovine milk protein comprises two major components: acid soluble whey protein and acid insoluble casein, with the latter representing about 80% of the total protein content of bovine milk. Upon entering the acidic environment of the stomach, casein precipitates and complexes with minerals forming semi-solid curds of varying size and firmness. Softer, smaller curds are easier for the body to digest than larger, harder curds. Curd formation may be an important consideration in the development of nutritional compositions, including, but not limited to infant formulas, medical foods, and premature infant formulas. In an embodiment of the present invention, the composition of the invention provides a nutritional composition having softer and smaller curds than standard infant formulas.

As discussed above, in certain embodiments, the nutritional composition of the invention also contains a functional protein such as TGF-β. In a particular embodiment of the invention, the level of TGF-β in the inventive composition is from about 0.0150 (pg/μg) ppm to about 0.1000 (pg/μg) ppm. In another embodiment, the level of TGF-β in the inventive composition is from about 0.0225 (pg/μg) ppm to about 0.0750 (pg/μg) ppm.

In a particular embodiment of the invention, the level of TGF-β in the inventive composition is from about 2500 pg/mL to about 10,000 pg/mL composition, more preferably from about 3000 pg/mL to about 8000 pg/mL.

In one embodiment, the ratio of TGF-β1:TGF-β2 in the inventive composition is in the range of about 1:1 to about 1:20, or, more particularly, in the range of about 1:5 to about 1:15.

In some embodiments, the bioactivity of TGF-β in a nutritional composition is enhanced by the addition of a bioactive-enriched whey fraction bioactive whey fraction. In an embodiment, this bioactive whey fraction may be a whey protein concentrate. In a particular embodiment, the whey protein concentrate may be Salibra® 800, available from Glanbia Nutritionals. In another embodiment, the whey protein concentrate may be Nutri Whey 800, available from DMV International. In yet another embodiment, the whey protein concentrate may be Salibra-850, available from Glanbia Nutritionals. In still another embodiment, the whey protein concentrate may be Prolacta Lacatalis WPI90, available from Lactilus Industrie U.S.A., Inc. In a further embodiment, the whey protein concentrate may be supplied by MG Nutritionals.

In some embodiments, the composition of the invention induces oral tolerance. As used herein, the term "oral tolerance" refers to the specific suppression of cellular and/or humoral immune responses to an antigen by prior administration of the antigen by the oral route. Oral tolerance affects the responsiveness of the local immune system in the intestinal mucosa itself, thus preventing hypersensitivity reactions to food proteins that could otherwise elicit potent inflammatory reactions in the gut. Development of oral tolerance is an important component in appropriate mucosal immune function. Oral antigens, like food, food proteins, or commensal bacteria, are normally processed in a manner that results in a regulated immune response. This response does not injure the host and results in systemic hypo-responsiveness in subsequent oral challenge with the same food antigen. Thus oral tolerance is established. Oral tolerance can fail, however, in response to the development and pathogenesis of several immunologically based diseases, including inflammatory bowel disease, Crohn's disease, and ulcerative colitis. In a particular embodiment, the combination of TGF-β and the prebiotics of the present invention may synergistically contribute to the induction and/or promotion of oral tolerance to antigens in circumstances where oral tolerance has previously failed. In some embodiments, the induction of oral tolerance may be enhanced by administration of the composition of the invention. In other embodiments, the oral tolerance acquired by a subject may be promoted or maintained by administration of the composition of the invention.

The following example describes an embodiment of the present disclosure. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE

This example illustrates an embodiment of a powdered infant formula of the present disclosure.

| Ingredients | |
|---|---|
| Ingredient | Amount per 100 kg |
| Lactose, Grind A | 35.119 kg |
| Palm Olein Oil | 12.264 kg |
| Coconut Oil | 5.451 kg |
| Soy Oil | 5.451 kg |
| High Oleic Sunflower Oil | 4.088 kg |
| Non-Fat Dry Milk, Medium-Heat, Spray Dried | 14.667 kg |
| Whey Protein Concentrate, 35% Protein, Super Sack | 14.667 kg |
| Galacto-Oligosaccharide Syrup (77% solids, 44% fiber) | 3.477 kg |
| Polydextrose Power (96% total solids, 96% carbohydrate, 86% fiber) | 1.770 kg |
| Calcium Gluconate, Monohydrate | 1.606 kg |
| Single Cell Arachidonic Acid Oil | 0.347 kg |
| Single Cell Docosahexaenoic Acid Oil | 0.238 kg |
| Choline Bitartrate | 0.228 kg |
| Potassium Chloride | 0.198 kg |
| Sodium Chloride | 24.780 g |
| Magnesium Oxide, Light | 22.790 g |
| L-Carnitine | 9.910 g |
| Ascorbic Acid | 156.687 g |
| Inositol | 39.887 g |
| Corn Syrup Solids | 35.478 g |
| Taurine | 33.875 g |
| Dry vitamin E Tocopheryl Acetate, 50% | 25.279 g |
| Vitamin A Palmitate, Dry Beadlets, CW Dispersible, 250 | 7.871 g |
| Niacinamide | 6.475 g |
| Vitamin K1 Dry Phytonadione USP Powder, 1% | 5.454 g |
| Calcium Pantothenate | 3.299 g |
| Vitamin $B_{12}$, 0.1% in starch | 2.122 g |
| Biotin Trituration, 1% | 1.608 g |
| Vitamin $D_3$ Powder | 0.969 g |
| Riboflavin | 0.755 g |
| Thiamine Hydrochloride | 0.601 g |
| Pyridoxine Hydrochloride | 0.518 g |
| Folic Acid | 0.122 g |
| Corn Syrup Solids | 192.187 g |
| Ferrous Sulfate, Heptahydrate | 49.600 g |
| Ascorbic Acid | 6.213 g |
| Malto-Dextrin | 146.096 g |
| Cytidine 5'-Monophosphate, Free Acid | 11.604 g |
| Uridine 5'-Monophosphate, Disodium Salt | 3.419 g |
| Adenosine 5'-Monophosphate, Free Acid | 2.711 g |
| Guanosine 5'-Monophosphate, Disodium Salt | 2.170 g |
| Lactose, Grind A | 138.017 g |

-continued

| Ingredients | |
|---|---|
| Ingredient | Amount per 100 kg |
| Zinc Sulfate, Monohydrate | 16.422 g |
| Corn Syrup Solids | 3.616 g |
| Sodium Selenite, Anhydrous | 0.018 g |
| Cupric Sulfate, Powder (CuSO$_4$•5H$_2$O) | 1.688 g |
| Manganese Sulfate, Monohydrate | 0.239 g |

| Proximate Analysis | | | |
|---|---|---|---|
| | Grams per 100 g | Grams per 100 mL at Normal Dilution | Caloric Distribution |
| Protein | 10.84 | 1.47 | 8.50 |
| Fat | 28.57 | 3.89 | 50.67 |
| Carbohydrate | 54.87 | 7.46 | 40.83 |
| Ash | 2.70 | 0.37 | |
| Moisture | 3.02 | 89.9 | |
| Calories | 508 | 69.1 | |

| Nutrients | |
|---|---|
| Nutrient | Quantities per 100 Calories |
| Calories | 100 |
| Protein, g | 2.1 |
| Fat, g | 5.6 |
| Carbohydrates, g | 10.6 |
| Ash, g | 0.6 |
| Water, mL (normal dilution) | 133 |
| Linoleic Acid, mg | 900 |
| α-Linolenic Acid, mg | 85 |
| Arachidonic Acid, mg | 25 |
| Docosahexaenoic Acid, mg | 17 |
| Vitamin A, IU | 300 |
| Vitamin D, IU | 60 |
| Vitamin E, IU | 2 |
| Vitamin K, mcg | 8 |
| Thiamin, mcg | 80 |
| Riboflavin, mcg | 140 |
| Vitamin B$_6$, mcg | 60 |
| Vitamin B$_{12}$, mcg | 0.3 |
| Niacin, mcg | 1000 |
| Folic Acid, mcg | 16 |
| Pantothenic Acid, mcg | 500 |
| Biotin, mcg | 3 |
| Vitamin C, mg | 12 |
| Choline, mg | 24 |
| Inositol, mg | 6 |
| Taurine, mg | 6 |
| Carnitine, mg | 2 |
| Calcium, mg | 78 |
| Phosphorus, mg | 43 |
| Magnesium, mg | 8 |
| Iron, mg | 1.8 |
| Zinc, mg | 1 |
| Manganese, mcg | 15 |
| Copper, mcg | 75 |
| Iodine, mcg | 10 |
| Sodium, mg | 27 |
| Potassium, mg | 108 |
| Chloride, mg | 63 |
| Selenium, mcg | 2.8 |
| Polydextrose | 0.3 |
| Galacto-oligosaccharide | 0.3 |
| AMP Equivalents, mg | 0.5 |
| CMP Equivalents, mg | 2.5 |

-continued

| Nutrients | |
|---|---|
| Nutrient | Quantities per 100 Calories |
| GMP Equivalents, mg | 0.3 |
| UMP Equivalents, mg | 0.9 |
| Nucleotide Equivalents, mg | 4.2 |

To prepare 1 liter of product at standard dilution (20 kcal/fl. oz.), 136 grams of powder was mixed with 895.2 grams of water. To prepare 1 quart of product at standard dilution, 128.7 grams of powder was mixed with 847.2 grams water.

Upon reconstitution, the infant formula described in this example contains approximately 2 g/L of galacto-oligosaccharide and 2 g/L of polydextrose. The infant formula has an ARA level of 25 mg/100 kcal. The formula contains 5.6 g fat/100 kcal, to achieve a fat content which is similar to human milk. The formula additionally has a low buffer strength.

All pH adjustments with regard to this infant formula were made with solutions of potassium hydroxide. The specific gravity of the formula is 1.03117.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A nutritional composition for an infant or child comprising
   a. a lipid or fat;
   b. a bovine milk protein source;
   c. about 5 to about 100 mg/100 kcal of a source of long chain polyunsaturated fatty acids which comprises docosahexanoic acid;
   d. about 0.1 to about 1 mg/100 kcal of a prebiotic composition, wherein the prebiotic composition comprises at least 20% of an oligosaccharide which has a fermentation rate which is demonstrably slower than that of a galacto-oligosaccharide; and
   e. about 0.0225 ppm to about 0.0750 ppm of TGF-β.

2. The nutritional composition of claim 1, wherein the source of long chain polyunsaturated fatty acids further comprises arachidonic acid.

3. The nutritional composition of claim 2, wherein the ratio of arachidonic acid to docosahexanoic acid is from about 1:3 to about 9:1.

4. The nutritional composition of claim 1, wherein the lipid or fat is present at a level of up to about 7 g/100 kcal.

5. The nutritional composition of claim 4, wherein the lipid or fat is present at a level of about 3 g/100 kcal to about 7 g/100 kcal.

6. The nutritional composition of claim 1, wherein the protein source is present at a level of up to 5 g/100 kcal.

7. The nutritional composition of claim 6, wherein the protein source is present at a level of about 1 to 5 g/100 kcal.

8. The nutritional composition of claim 1, wherein the oligosaccharide which has a fermentation rate which is demonstrably slower than that of galacto-oligosaccharide comprises polydextrose.

9. The nutritional composition of claim 8, wherein the prebiotic composition further comprises galacto-oligosaccharide.

10. The nutritional composition of claim 1, which further comprises at least one probiotic.

11. The nutritional composition of claim 10, wherein the probiotic is selected from the group consisting of *Bifidobacteria* spp., *Lactobacillus* spp and combinations thereof.

12. The nutritional composition of claim 1, which comprises an infant formula.

13. The nutritional composition of claim 1, which further comprises a bioactive-enhanced whey fraction.

14. The nutritional composition of claim 1, wherein the combination of TGF-$\beta$ and the prebiotic synergistically contributes to the induction of oral tolerance to antigens in circumstances where oral tolerance has previously failed.

* * * * *